United States Patent [19]

Juergens

[11] Patent Number: 5,200,909
[45] Date of Patent: Apr. 6, 1993

[54] METHOD FOR EVALUATION OF A LIQUID, PARTICULARLY WINE

[76] Inventor: John P. Juergens, 3011 Hillmont Dr., Oxford, Miss. 38655

[21] Appl. No.: 629,644

[22] Filed: Dec. 7, 1990

Related U.S. Application Data

[63] Continuation-in-part of Ser. No. 316,667, Feb. 28, 1989, abandoned.

[51] Int. Cl.$^5$ .......................................... G01N 33/14
[52] U.S. Cl. .................................... 364/497; 364/401; 364/403; 364/551.01; 436/24
[58] Field of Search ........... 364/401, 403, 497, 551.01; 436/24

[56] References Cited

PUBLICATIONS

Don Blackburn, "Describing Wine Structure Clearly", Practical Winery, Grapegrowing and Winemaking Review, vol. 6, No. 5, Jan./Feb., 1986.
"Chemistry of Wine Making", Symposium sponsored by the Division of Agriculture and Food Chemistry at the 165th Meeting of the American Chemical Society, Dallas, Tex., Apr. 12-13, 1973, Advances in Chemistry Series 137, pp. 134-150, 185-211.
"Official Methods of Analysis of the Association of Official Analytical Chemists", Association of Official Analytical Chemists, Inc., Arlington, Virginia (Fourteenth Edition, 1984), pp. 187-188, 221-230.
"Official Methods of Analysis of the Association of Official Analytical Chemists", Association of Official Analytical Chemists, Inc., Arlington, Va. (1980), pp. 180-181, 513-516, 942-943.
Ough et al., "Methods for Analysis of Musts and Wines", John Wiley & Sons, New York, 1988, pp. 1-6, 42-45, 58-59, 61-62, 66, 69-71, 83, 105, 108, 121, 125-139, 202, 204-208, 212-213, 217-221.

*Primary Examiner*—Edward R. Cosimano
*Attorney, Agent, or Firm*—Staas & Halsey

[57] ABSTRACT

A method and apparatus for classifying wine by chemically analyzing a wine sample to determine content values indicative of amounts of constituents in the wine sample, evaluating potential interaction among constituents in the wine sample, converting the content value of each of the constituents to a scaled value adjusted for interaction with the other constituents, the scale to which each of the content values is converted being equal in size, and displaying the scale values so that palatability factors for the sampled wine can be determined by viewing the display.

19 Claims, 12 Drawing Sheets

WINE COLOR

|  | WHITE | RED | BLUSH |
|---|---|---|---|
| BODY | 2 | 2 | 1 |
| ACID/TARTNESS | 3 | 2 | 1 |
| TANNIN/ASTRINGENCY | 1 | 3 | 2 |
| SWEETNESS | 3 | 3 | 3 |

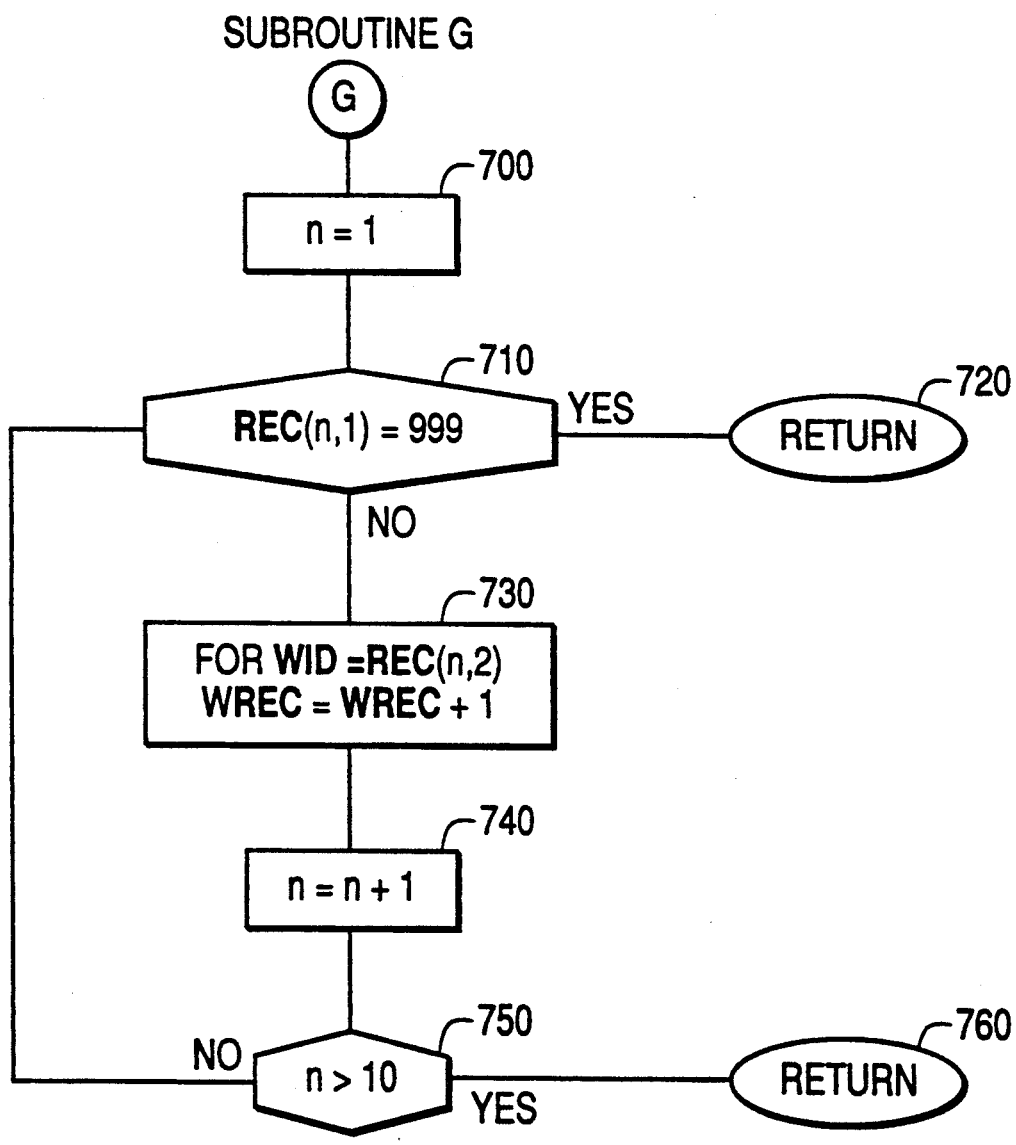

METHOD FOR EVALUATION OF A LIQUID, PARTICULARLY WINE

This application is a continuation-in-part of application Ser. No. 07/316,667, filed Feb. 28, 1989, now abandoned.

BACKGROUND OF THE INVENTION

1. Field of the Invention

This invention relates to a method and apparatus for evaluating a liquid, particularly wine, based upon constituents therein, and more particularly, to a method and apparatus for chemically evaluating various properties of a liquid and converting the data derived by the evaluation to a standard scale so that a consumer may make an objective evaluation of the liquid based on viewing the display.

2. Description of the Related Art

Consumers rely on labels when making consumer decisions to determine the contents of items being purchased so that they may evaluate whether the item appeals to them. Information on wine labels, for example, if provided at all, usually provides only subjective and frequently abstract written descriptions of one or several characteristics of the wine, for example, aroma, flavor, sweetness, astringency, or body. Occasionally, additional information is provided regarding the technique used in making the wine, proper serving temperature for the wine, and guidance on the types of food the wine will best accompany.

The subjective descriptions noted above are of limited value to the great majority of wine consumers, particularly the inexperienced wine consumer. The descriptions are developed by individuals who are highly trained and very experienced in wine evaluation. Thus, these subjective interpretations of wine characteristics are generally too abstract and sophisticated for the average inexperienced consumer. Additionally, taste perceptions vary among individuals, even among experienced judges. Thus, the subjective information appearing on wine labels can vary according to the taste perception of the judge making the evaluation.

Furthermore, interactions may occur among some of the chemical constituents in wine such that taste perceptions may be altered and therefore may not be directly related to the absolute quantities of each constituent present. For these reasons, under current labeling practice, even the most extensive description for a particular wine, including that which displays quantitative data or scales based on quantitative data, does not provide the consumer with the kind of objective, understandable information necessary to make a confident, informed wine purchase decision.

SUMMARY OF THE INVENTION

It is an object of the present invention to provide an easily understandable, quantitative assessment of the characteristics of a liquid, for example, wine.

Another object of the present invention is to provide an easily understandable, quantitative assessment of the characteristics of a liquid, for example, wine, in which the characteristics of the liquid are evaluated, including interactions among the chemical constituents, and the data resulting from the evaluation is converted to a graphic display.

It is an additional object of the present invention to provide an easily understandable, quantitative assessment of the characteristics of a liquid, for example, wine, in which the characteristics are chemically evaluated, including interactions among the chemical constituents, and the data resulting from the evaluation is converted to a graphic display, with each of the characteristics being displayed on separate, equal scales.

It is also an object of the present invention to provide a method which provides the quantitative assessment of wine discussed above.

It is a further object of the present invention to provide a method which will allow consumers to easily identify preferential wines.

According to the present invention, there is disclosed a method for classifying wine, comprising the steps of: chemically analyzing a wine sample to determine a plurality of content values indicative of amounts of a plurality of constituents in the wine sample; evaluating potential interaction among constituents in the wine sample; converting the content value of each of the plurality of constituents to a scaled value adjusted for interaction with other constituents, the scale to which each of the content values is converted being equal in size; and displaying the scale values so that a plurality of palatability factors for the sampled wine can be determined by viewing the display. Also disclosed are apparatus for performing the above method.

These together with other objects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 14 is a flowchart diagram of a subroutine for updating a wine data file in accordance with the embodiment of FIG. 8.

DESCRIPTION OF THE PREFERRED EMBODIMENT

Figure 1:
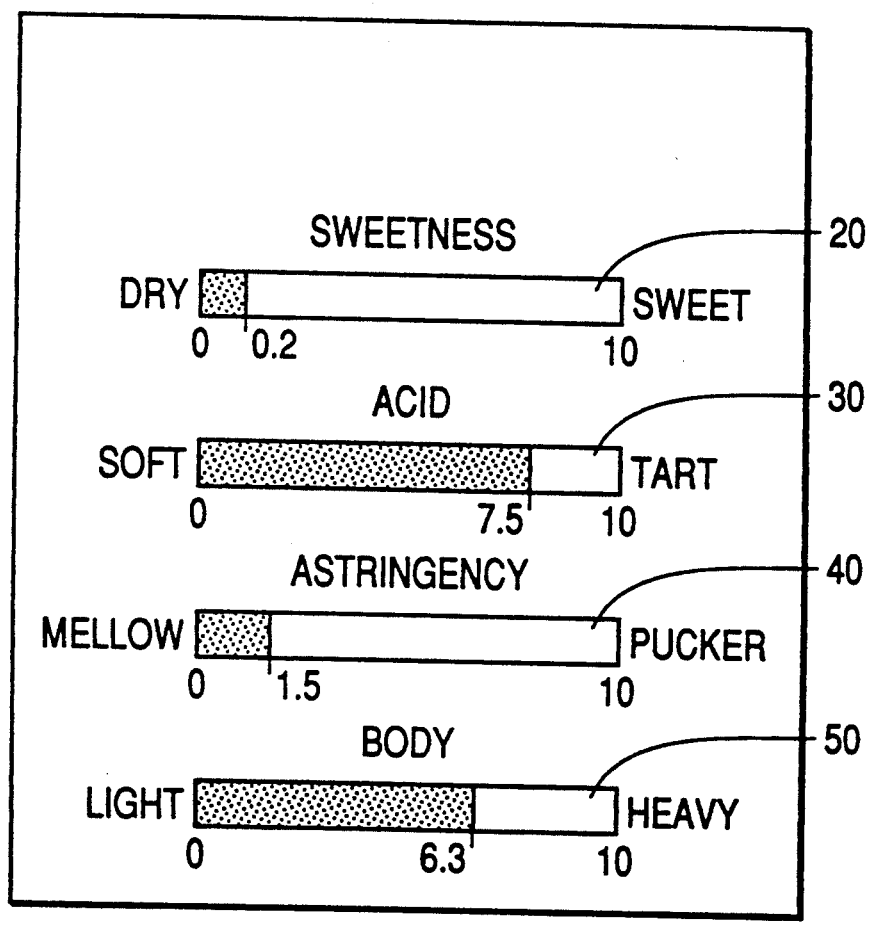
FIG. 1 is an example of a bar chart for graphically displaying various characteristics in accordance with a first embodiment of the present invention.

To understand the disclosed method, an understanding of the basic characteristics evaluated when choosing wine is necessary.

In arriving at the disclosed method of wine evaluation, a three-step research process for development of the wine evaluation and labeling system was conducted. The three steps are:

1) determining the most important characteristic in consumer's wine preferences and purchase decisions;

2) determining whether those characteristics are linked to wine constituents which can be quantitatively determined, and making the quantitative determinations; and 3) converting the quantitative determinations to readily understandable rating scales which correlate those characteristics important to consumers with the objective laboratory data.

The most important characteristics in consumers wine preference and purchase decisions (step 1) were determined by a review of the literature and by using consumer panel research techniques. The results of the consumer panel tests reveal that sweetness, tartness (acidity), astringency and body are the most important characteristics of wine to consumers. The results of the consumer panel test were found to be consistent with data published in several reference texts on the sensory evaluation of wine and food (see, for example, *Wines: Their Sensory Evaluation*, by Maynard A. Amerine and Edward B. Roessler, W. H. Freeman & Co., 1976, and *Principles of Sensory Evaluation of Food* by Manyard A. Amerine, Rose Marie Pangborn and Edward B. Roessler, Academic Press, 1965). The literature indicated that the above characteristics ar fundamentally the most important in evaluating the quality of wine; the consumer research demonstrated that the same characteristics played a most important role in consumers preferences and wine purchases.

The next step was to determine whether the characteristics identified in step 1 were linked to quantifiable wine constituents (step 2). According to the above-mentioned references and others, including *The Fine Wines of California*, Robert S. Blumberg & Hurst Hannum, Dolphin Books, 1973; Alexis Lichine's *Encyclopedia of Wines and Spirits* (in collaboration with William Fifield and with the assistance of Jonathan Bartlett and Jane Stockwood), Alfred A. Knopf, Inc., 1972; *Chemistry of Wine Making*, Symposium sponsored by the Division of Agricultural and Food Chemistry at the 165th Meeting of the American Chemical Society, Dallas, Tex., Apr. 12–13, 1973, Advances in Chemistry Series 137, the following relationships have been determined through empirical research:

1) Sweetness is directly related to the amount of reducing sugars (principally glucose and fructose) in the wine;

2) Acidity or tartness is directly related to the pH and to a lesser degree, the titratable acids in the wine;

3) Astringency is directly related to the amount of polyphenol compounds (principally the tannins) in the wine; and 4) Body is principally related to the relative amounts of ethanol, sugar and tannins in the wine.

All of the above constituents (reducing sugars, pH and titratable acids, polyphenol compounds and ethanol) are constituents which can be quantified through objective laboratory measurements. Various methods for analyzing wines to determine the above-identified characteristic constituents are described in *Chemistry of Wine Making*, supra, and *Official Methods of Analysis of the Association of Official Analytical Chemists*, published by the Association of Official Analytical Chemists, Inc., Arlington, Vir. (14th Edition, 1984). In addition, wine samples can be sent to laboratories for evaluation, for example, Scott Laboratories, Inc. in Petaluma, CA; ETS Laboratories in St. Helena, CA; and VINQUIRY Winemakers Service and Research Laboratory in Healdsburg, Calif.

It was also discovered through empirical research that interactions may occur among the above constituents which alter the perception of the intensity of the individual constituents and characteristics. For example, high levels of polyphenol compounds (principally tannins) and high acidity each ca reduce the apparent sweetness of wine. Furthermore, the interaction between sugar and polyphenol compounds (principally tannins) is reciprocal, that is, high levels of sugar can reduce the perceived intensity of polyphenol compounds (principally tannins) and consequently reduce the perceived astringency. High acidity can also diminish the perceived body of wine through its influence on apparent sweetness and by virtue of its palate cleaning action. These interactions are continuous across the respective scales; however, consumers will have varying sensitivities or thresholds of detection for changes in the intensity of the constituents and characteristics involved. The effects of these interactions are most noticeable when one interacting constituent is present in low to moderate amounts and one or more of the other interacting constituents are present in relatively high amounts.

Finally, the disclosed method requires conversion of the laboratory results to readily understandable scales and correlation of the important characteristics with objective laboratory measurements of the constituents responsible for those characteristics, including adjustment for interaction among the constituents (step 3). This is achieved by creating individual scales, each of 0–10 units, to express the degrees of the characteristics, e.g., sweetness, acidity, astringency, and body, in the wine. The 0 and the 10 of the scale represent the lowest and highest degree of each characteristic, respectively. The low figure, 0, can represent the lowest value one would expect in an ordinary table wine. For example, according to the literature, the low value for tannin/astringency has been determined to be 120 milligrams (mg) per liter for an ordinary table wine. Thus, any wine having a value of 120 mg per liter of astringency or less, receives a 0 rating for the 0-10 scale. On the other end of the spectrum, it has been determined that a tannin/astringency value of 3000 mg per liter or greater is beyond the level found in an ordinary table wine. Thus, a wine having a tannin/astringency value of 3000 mg per liter or more receives a 10 rating. Values falling between 120 mg and 3000 mg of tannin/astringency are given a value between zero and 10 based upon their tannin/astringency level. For example, a level of 1560 mg per liter of tannin/astringency, which is halfway between 120 mg and 3000 mg, is given a scale rating of five. Formulas, discussed below, were derived to convert the raw laboratory data into the scale values.

In a first embodiment, the scales are presented graphically in the form of a bar chart, with numerical values ranging from 0-10. FIG. 1 is an example of one such bar chart, which can be applied to a wine bottle or incorporated in a label, for example. The sweetness scale 20 indicates a sweetness level of 0.2. The acidity scale 30 indicates an acidity level of 7.5. The astringency scale 40 indicates a tannin level of 1.5. The body scale 50 indicates a body level of 6.3.

The following equations and scales were derived for determining an alcohol scale, an acid/tartness scale, a tannin/astringency scale, a sweetness scale, and a body scale. The non-variables were derived based on the various high and low ranges defining an ordinary table wine. Obviously, if the ranges are changed, so will the non-variables.

A. Alcohol Scale

Figure 2:
FIG. 2 is a graph showing an alcohol scale in accordance with the embodiment of FIG. 1.

For determining the alcohol scale, in accordance with industry and legal standards, the wines having an alcohol content below 8% or above 15%, by volume, are not considered ordinary table wines by legal definition, and thus are off scale. This is graphically shown in FIG. 2. The values for equation:

$$S_{Alc} = 1.43 \times Ax - 11.43 \qquad (1)$$

where $S_{Alc}$=scale value for alcohol content and $Ax$ equals the laboratory value of alcohol content in percent by volume.

B. Acid/Tartness Scale

Figure 3:
FIG. 3 is a graph of an acid/tartness scale in accordance with the embodiment of FIG. 1.

FIG. 3 illustrates a sample scale for acid/tartness. For ordinary table wines, the industry accepted optimum range for pH is a pH level of 3.8 down to 3.0. A pH value above 3.8 is considered undesirable in a wine, as is a pH below 3.0. The following equation is used to determine the acid/tartness scale:

$$S_{pH} = 47.5 - 12.5 \times pHx \qquad (2)$$

where $S_{pH}$=the scale value for the acidity or tartness of the wine and where $pHx$ equals the laboratory value of the acidity in terms of pH units.

C. Tannin/Astringency Scale

Figure 4:
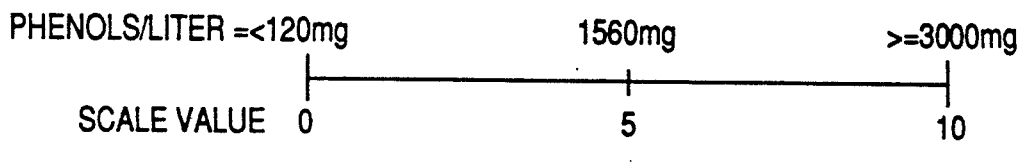
FIG. 4 is a graph of a tannin/astringency scale in accordance with the embodiment of FIG. 1.

FIG. 4 illustrates a scale for displaying the tannin/astringency level of a wine. The range of astringency values for an ordinary table wine is from 120 mg per liter to 3000 mg per liter (total phenols). The basic equation for determining the position on the scale of the tested wine is as follows:

$$S_T = 0.625 + (0.00313) Tx \qquad (3)$$

where $S_T$=scale value for tannin/astringency; and $Tx$ equals laboratory value for tannin, expressed as total phenols.

An elevated sugar level reduces the apparent astringency of wine; therefore, an adjustment in the astringency scale is necessary when the total reducing sugar level exceeds 2.0%. In this case, the following alternate formula is used to determine the Tannin/Astringency scale.

If reducing sugar content is greater than 2.0%, then:

$$S_T = (0.625 - 0.00313 Tx) \times (1.4 - 0.2 S_x) \qquad (4)$$

Where:

$S_T$=scale value for tannin/astringency $Tx$=laboratory value for tannin, expressed as total phenols $S_x$=laboratory value for the percent of reducing sugars greater than 2.0%).

When the reducing sugar content of the wine does not exceed 2.0% the correction term is dropped from the equation and the basic equation for astringency determination shown above is used. This threshold level is an approximation which was established through empirical research of the inventor. It is likely that some consumers may have greater or less sensitivity to the interactive effects and may detect changes in the perceptions of astringency at different threshold levels. However, this criterion level accounts for most of the alternation in perception due to this interaction.

D. Sweetness Scale

Figure 5:
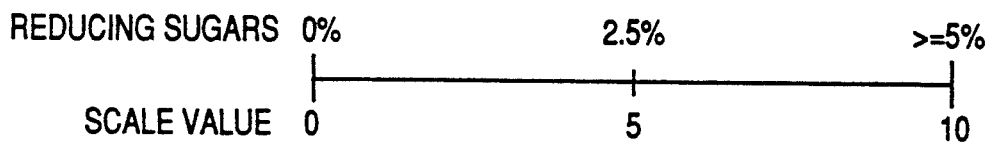
FIG. 5 is a graph of a sweetness scale in accordance with the embodiment of FIG. 1.

The accepted range of values on the sweetness scale for an ordinary table wine are from 0 percent to 5 percent total reducing sugars. FIG. 5 illustrates an example of a sweetness scale utilizing the 0-5 percent range. The basic equation for determining the scale is as follows:

$$S_s = 2 S_x \qquad (5)$$

where $S_s$=scale value for sweetness; $S_x$ equals laboratory value for the percent of reducing sugar content.

In order to adjust for the negative interaction of high acidity and a high tannin level on perceived sweetness, the following alternate formula is used to determine the sweetness scale.

High acidity is defined as a pH less than 3.2 and a high tannin level is defined as total polyphenols greater than 2250 mg/liter. If these levels are exceeded, then:

$$S_x = (2 S_x) \times (0.3125 \, pHx) \times (3 - 0.0009 T_x) \qquad (6)$$

Where:

$S_s$=scale value for sweetness $S_x$=laboratory value for the percent of reducing sugar content $pHx$=laboratory value for acidity in terms of pH units (less than 3.2)

$T_x$=laboratory value for tannin, expressed as total polyphenols (greater than 2250 mg/liter).

The respective correction terms for acid and tannin drop from the equation when the criterion levels of pH=3.2 and tannin=2250 mg/liter are not exceeded. When neither of these constituents reach these critical values, the sweetness scale determination reverts to the basic equation shown above. These threshold levels are approximations which were established through empirical research of the inventor. It is likely that some consumers will have greater or less sensitivity to the interactive effects and may detect sweetness intensity changes at different threshold levels. However, these criterion levels account for most of the alteration in perception due to these interactions.

E. Body Scale

Figure 6:
FIG. 6 is a graph of a body scale in accordance with the embodiment of FIG. 1.

FIG. 6 is a graph of a body scale in accordance with the embodiment of FIG. 1. The body of a wine is determined primarily by the amount of sugars, alcohol and total phenols (tannins) present in the wine. Therefore, the body scale is derived from the 0–10 scale values for sugar, alcohol and tannins. However, adjustments must be made to the body scale when any of these components (sugars, alcohol and tannins) differ substantially from certain points on their respective scales. To accommodate these adjustments, there are four different formulas A-D for body scale $(S_s)$ determination, depending upon the scale value of tannin and sugars in the wine.

Body Scale A: If Tannin Scale $(S_T) < 4$ and Sweetness Scale $(S_S) = < 3$, then:
$$S_B = (S_T + S_S + S_{Alc})/3 + (S_{Alc} - 5/1.43) + |3 - S_T| \quad (7)$$

Body Scale B: If Tannin Scale $(S_T) < 4$ and Sweetness Scale $(S_S) > 3$, then:
$$S_B = (S_T + S_S + S_{Alc})/3 + (S_{Alc} - 5/1.43) + \quad (8)$$
$$(S_S - 3) * 0.5 + |3 - S_T|$$

Body Scale C: If Tannin Scale $(S_T) >= 4$ and Sweetness Scale $(S_S) = < 3$, then:
$$S_B = (S_T + S_S + S_{Alc})/3 + (S_{Alc} - 5/1.43) + |5 - S_T| \quad (9)$$

Body Scale D: If Tannin Scale $(S_T) >= 4$ and Sweetness Scale $(S_S) > 3$, then:
$$S_B = (S_T + S_S + S_{Alc})/3 + (S_{Alc} - 5/1.43) + \quad (10)$$
$$(S_S - 3) * 0.5 + |5 - S_T|$$

As mentioned previously, acidity can influence the perceived body of wine through its interaction with sugar and directly due to its mouth or palate cleansing effect. Since the sweetness scale is a component of the body determination, the impact of high acidity through sweetness is accounted for. However, an additional direct correction factor is needed for the mouth cleansing effect of high acid. Since the body scales are derived from other component scales, the scale value for acidity is used to calculate this correction factor.

High acidity was defined as a pH less than 3.2 which is equivalent to a scale value of 7.5. Therefore, if the acidity scale value exceeds 7.5, the result of each of the preceding equations is multiplied by the following correction term:

$$2 - 0.133 S_{pH} \quad (11)$$

where:

$S_{pH}$ = scale value for acidity/tartness

When acidity levels do not exceed a scale value of 7.5 this term is not used and body determination reverts to the basic formulas above. As with the other corrections factors, this threshold level also is an approximation which was established through empirical research of the inventor. It is likely that some consumers may have greater or less sensitivity to the interactive effects and may detect changes in the body at a different threshold level. However, this criterion level accounts for most of the alteration in perception due to this interaction.

As noted above, the scale values for each wine can be displayed in graphic form as shown, for example, in FIG. 1. This display allows a consumer to evaluate a wine and decide if it has desirable characteristics as discerned by their individual taste perception merely by reading the display.

The following examples illustrate the conversion of raw laboratory measurement data to scale values in accordance with the first embodiment.

EXAMPLE 1

A dry wine with medium body has the following laboratory values:

| Alcohol - 13.2% | Acid - pH 3.19 |
| --- | --- |
| Sugar - 0.1% | Tannin - 305 mg/Liter |
| Scale Values: | |
| Alcohol = | 7.4 |
| Sweetness = | 0.2 (corrected for high acidity) |
| Acid/Tartness = | 7.5 |
| Tannin/Astringency = | 1.5 |
| Body = | 6.3 (corrected for high acidity) |

EXAMPLE 2

A dry red wine with fairly light body has the following laboratory values:

| Alcohol - 12.0% | Acid - pH 3.34 |
| --- | --- |
| Sugar - 0.1% | Tannin 1000 mg/Liter |
| Scale Values: | |
| Alcohol = | 5.7 |
| Sweetness = | 0.2 |
| Acid/Tartness = | 5.8 |
| Tannin/Astringency = | 3.8 |
| Body = | 4.5 |

EXAMPLE 3

A somewhat sweet, but acidic rose or blush wine has the following laboratory values:

| Alcohol - 11.0% | Acid - pH 2.92 |
| --- | --- |
| Sugar - 3.0% | Tannin - 470 mg/Liter |
| Scale values: | |
| Alcohol = | 4.3 |
| Sweetness = | 5.5 (corrected for high acidity) |
| Acid/tartness = | 10 |
| Tannin/Astringency = | 1.7 (corrected for high sugar content) |
| Body = | 3.8 (corrected for high acidity) |

EXAMPLE 4

A very dry, heavy red wine has the following laboratory values:

| Alcohol - 13.5% | Acid - pH 3.61 |
| --- | --- |
| Sugar - 0.2% | Tannin - 2345 mg/Liter |
| Scale Values: | |
| Alcohol = | 7.9 |
| Sweetness = | 0.36 (corrected for high tannin level) |
| Acid/Tartness = | 2.4 |
| Tannin/Astringency = | 8.0 |
| Body = | 10 |

The scale values are presented graphically as shown in FIG. 1. The rating shown in FIG. 1 is for the wine in Example 1.

Figure 7:
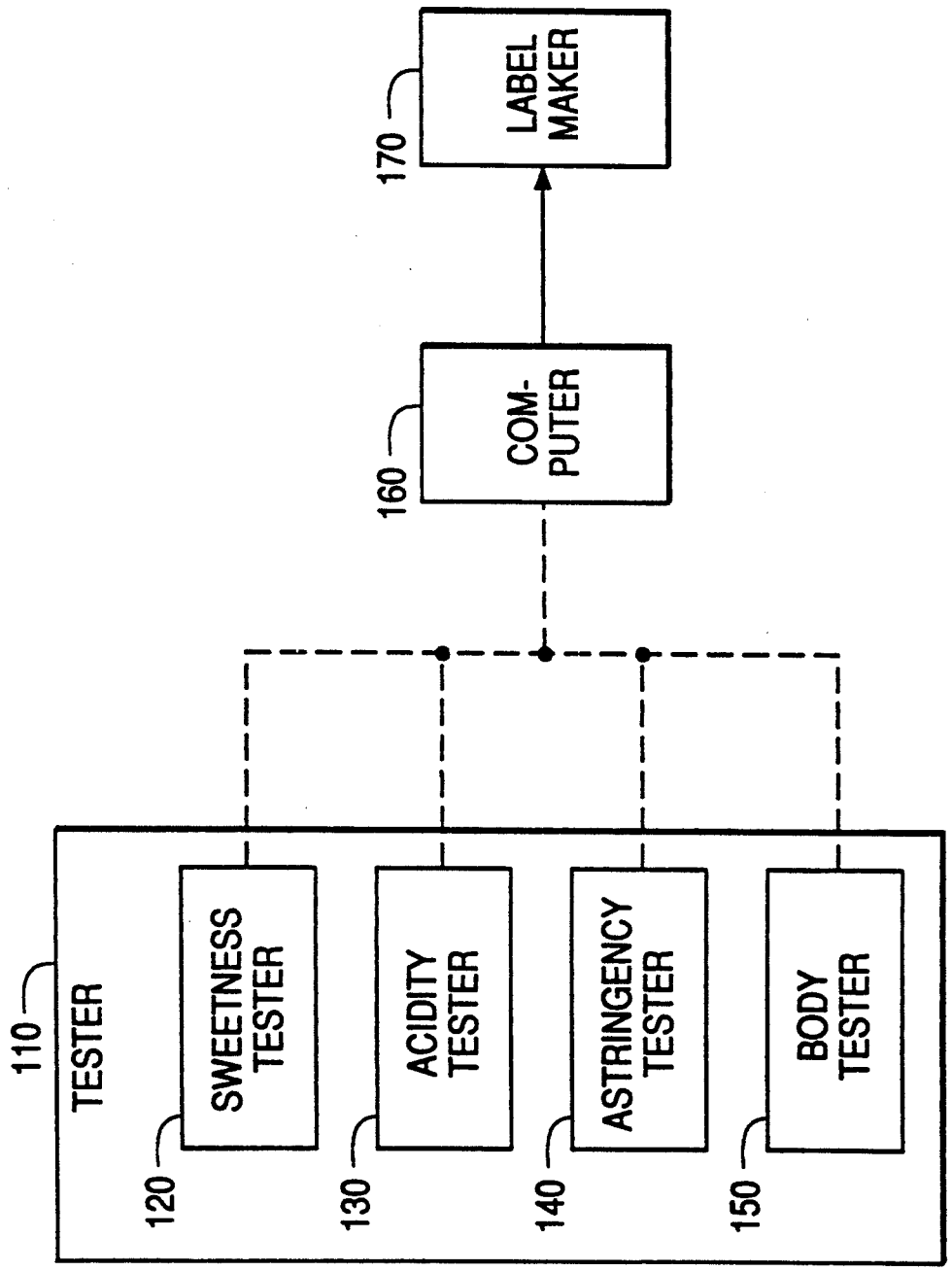
FIG. 7 is a block diagram of an apparatus for performing the method of the first embodiment.
Figure 7A:
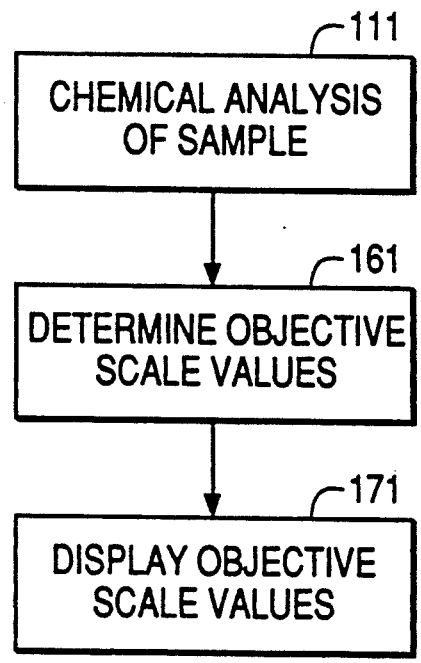
FIG. 7A is a flowchart diagram of steps for performing the method of the first embodiment.

FIG. 7 is a block diagram of an apparatus for performing the method of the first embodiment. FIG. 7A is a flowchart diagram of steps for performing the method of the first embodiment. Testing device 110 is a testing means for testing the wine sample to determine the amount of the measurable constituents in the sample (step 111 in FIG. 7A). For example, testing device 110 comprises a sweetness tester 120, an acidity tester 130, an astringency tester 140 and a body tester 150. The wine sample is tested by the testing device 110, and the results of the test are input to computer 160. These testers can be any conventional testing devices. For example, the analysis methods described above can be used and then the results can be manually input to the computer 160 via a keyboard. Alternatively, the entire system could be automated, with testing devices being directly connected to the computer 160 so as to provide the test results directly to the computer. Computer 160 performs the necessary calculations to develop the above-mentioned scale values (step 171 in FIG. 7A), and converts the scale values to a data format for graphically displaying the scales. The formatted data is output to label marker 170 (step 171 in FIG. 7A), which prints the labels which include the scales thereon.

In a second embodiment, the rating system is incorporated into an interactive computer program designed to assist consumers in identifying wines with the characteristics they desire at the point of purchase. For example, the program can be installed in a computer located in retail outlets for wines. The program is menu driven to allow the consumer to specify the characteristics desired within a given price range for wines stocked by that particular retailer. The program also permits the consumer to specify a wine with which he or she is familiar as a reference point. The program presents a list of wines with rating scales that possess the desired characteristics input or which are similar to the wines specified.

If the consumer specifies limits on any of the characteristics, the program will keep the wine selected within these limits. If the consumer does not specify limits on any of the characteristics, the program defaults to parameters which are, for example, plus or minus 1 scale unit for that particular characteristic. For example, a consumer might specify a wine having a sweetness level of between 3-6. Alternatively, if the consumer specifies a sweetness level of 4, the program can default to wines in the 3-5 sweetness range. Of course, the computer could also default so that it picks the precise value specified. Any parameter used by a consumer for selecting wine can be included, including the place of origin of the wine, the price, the grape type, etc.

FIGS. 8-10 and 12-15 are flowchart diagrams for an example of a computer program for implementing the wine evaluation and display system of the present invention.

Figure 8:
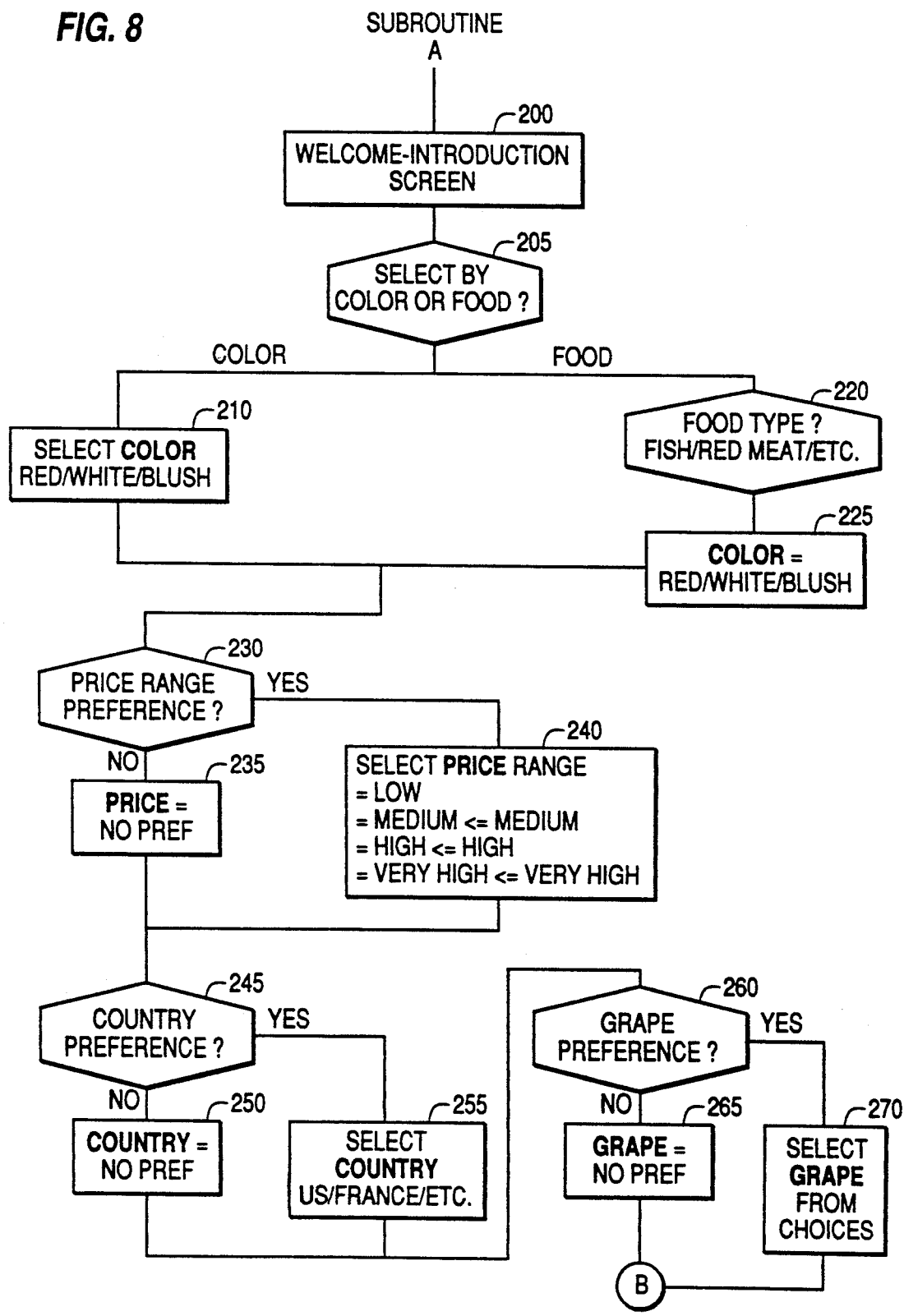
FIG. 8 is a flowchart diagram of a subroutine for a second embodiment of the present invention.

FIG. 8 is a flow chart diagram of a subroutine (subroutine A) which introduces the system to the user and allows the user to identify the variables to be used in arriving at the wine list of wines having the identified characteristics. For example, in FIG. 8, the user is first introduced to the system by a welcome-instruction screen (step 200) which contains informational descriptions of the system. The user then proceeds to step 205, where a particular color wine, or a particular type of food is input. The program automatically matches the particular food type with the conventionally recognized color wine that goes with that particular food type (steps 220 and 225) if the user inputs a food type. Alternatively, if the user has a wine color preference, the user inputs the preference at step 205, and the program selects that color as a limiter at step 210. The user can chose a price range, or opt not to limit the wine choice to any particular price range, at step 230. If the consumer chooses not to limit the wine to any price range, the program indicates NOPREF at step 235 and moves on to a country preference query at step 245. If the consumer does want to limit the price to a certain range, the program goes to select price range step 240, at which point the parameters of the range are input by the consumer. After the price range has been defined, the program moves on to the country preference query step 245.

If the consumer has a preference of country, the country is input at step 255. Otherwise, the consumer indicates no country preference (NOPREF) at step 250. Finally, at step 260, the user has the option of selecting a grape preference from a menu (step 270) or opt not to chose a grape type limiter (step 265). If the consumer chooses not to limit the wine to a grape type, the program indicates NOPREF at step 265 and moves on to subroutine B. Alternatively, if the consumer does want to limit the wine to a grape type, the program goes to select grape from choices step 270, at which point the consumer selects a grape preference from a menu. After the grape preference is selected, the program moves on to subroutine B.

Figure 9:
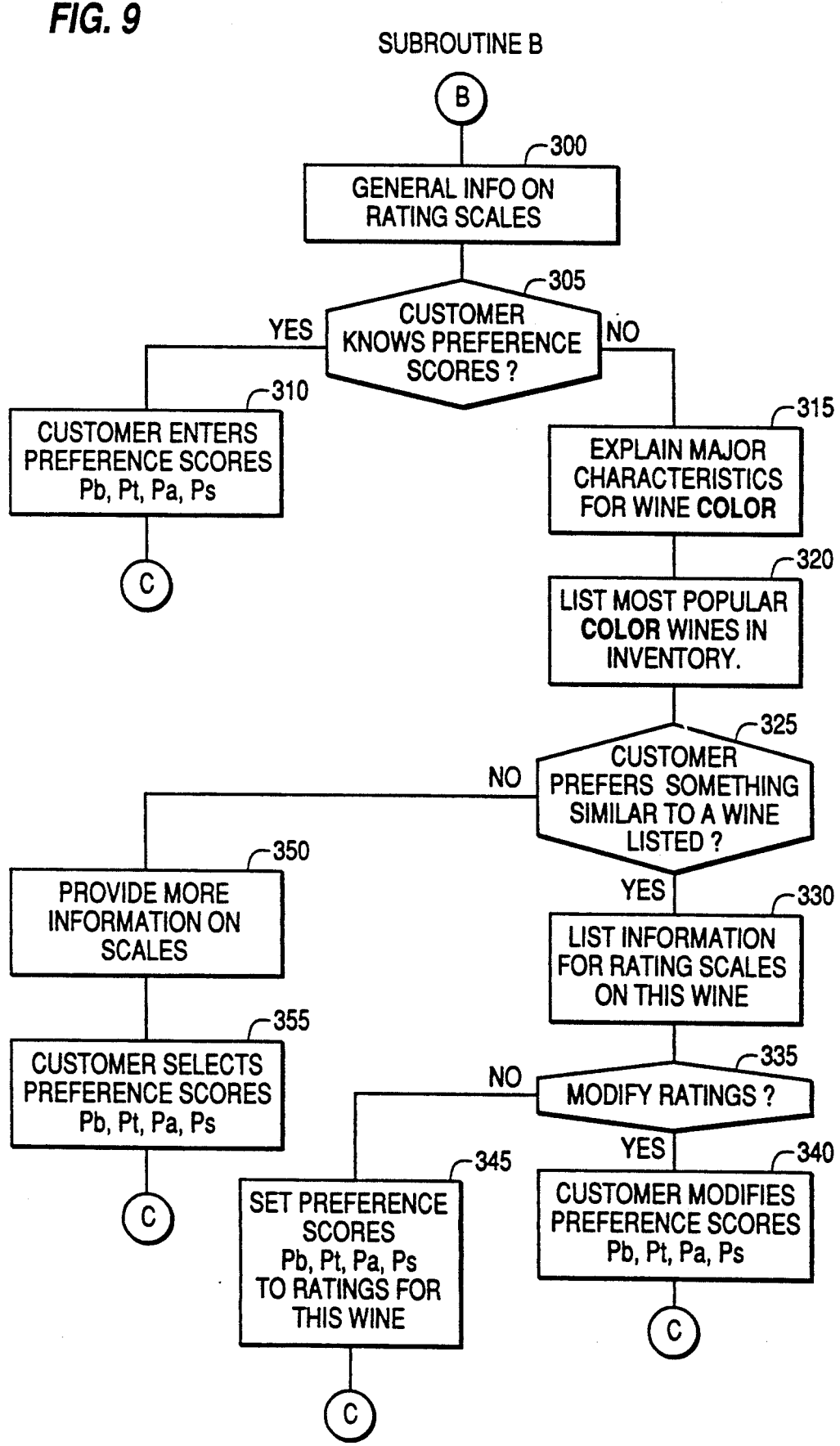
FIG. 9 is a flowchart diagram of a subroutine in accordance with the embodiment of FIG. 8 which enables a consumer to enter preferred rating scale values for wines.

Once through subroutine A of FIG. 8, the program moves to subroutine B. FIG. 9 is a flowchart diagram of subroutine B which enables a consumer to enter preferred rating scale values for wines if they are known, or, if the rating preference scales are not known, educates the consumer on various wine characteristics and their relation to the scales, and then allows the consumer to chose rating scale values (preference scores). Step 300 provides the consumer with general information on the rating scales, for example, definitions of the scale ranges and what they mean. In step 305, the consumer is asked to input whether or not preference scores are known. If the consumer answers yes, the consumer is requested to enter the preference scores in step 310 and the program moves on to subroutine C. If the consumer does not know his preference scores, the program moves to step 315 which displays a explanation of the major characteristics for wine color, and step 320 which displays a listing of the most popular color wines in the inventory. If the consumer decides that none of the wines on the list in step 320 are desirable, the customer inputs "NO" at step 325 and is then provided more information on the rating scales at step 350. The customer is then asked (355) to select preference scores for preferred body (Pb), preferred tannin (Pt), preferred astringency (Pa) and preferred sweetness (Ps).

If, however, at step 325, the consumer indicates that one of the wines listed in step 320 is desirable, the customer inputs "YES" and is given rating scale scores for that particular wine at step 330. At step 335, the consumer is given the option of modifying the rating scale score for that wine (step 340) or selecting the preference scores to be the same as the rating scale scores for the listed wine (step 345). If the consumer chooses to modify the rating scale scores for the listed wine at step 335, the program goes to step 340, at which point the customer modifies the rating scale scores. After the rating scale scores are modified, the program moves on to subroutine C. Alternatively, if the consumer chooses to select the preference scores to be the same as the rating scale scores for the listed wine at step 335, the program goes to step 345 and sets the preference scores to the rating scale scores for the listed wine. After the preference scores are set, the program moves on to subroutine C. The final result of subroutine B is that preference scores are chosen in accordance with the consumer's input. Once these preference scores are chosen, the program moves to subroutine C.

Figure 10A:
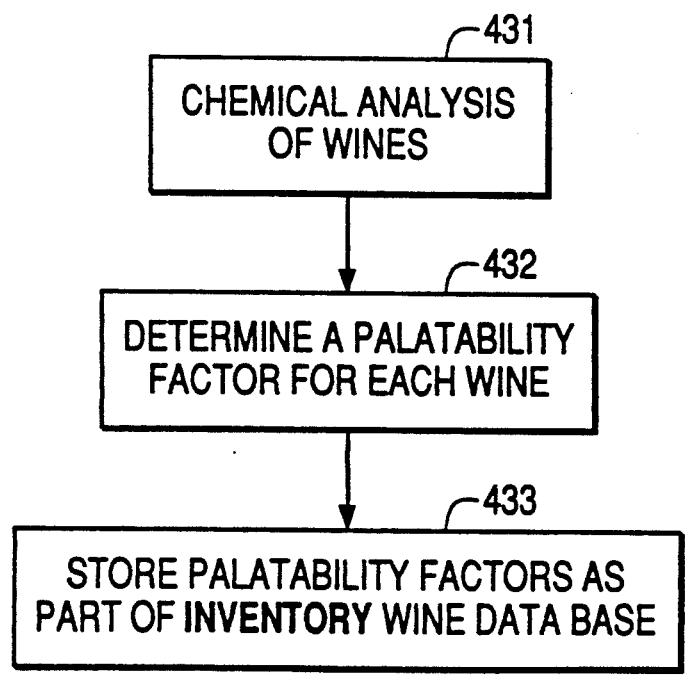
FIG. 10A is a flowchart diagram for storing palatability factors as part of an inventory wine database in accordance with the subroutine of FIG. 10.
Figure 10:
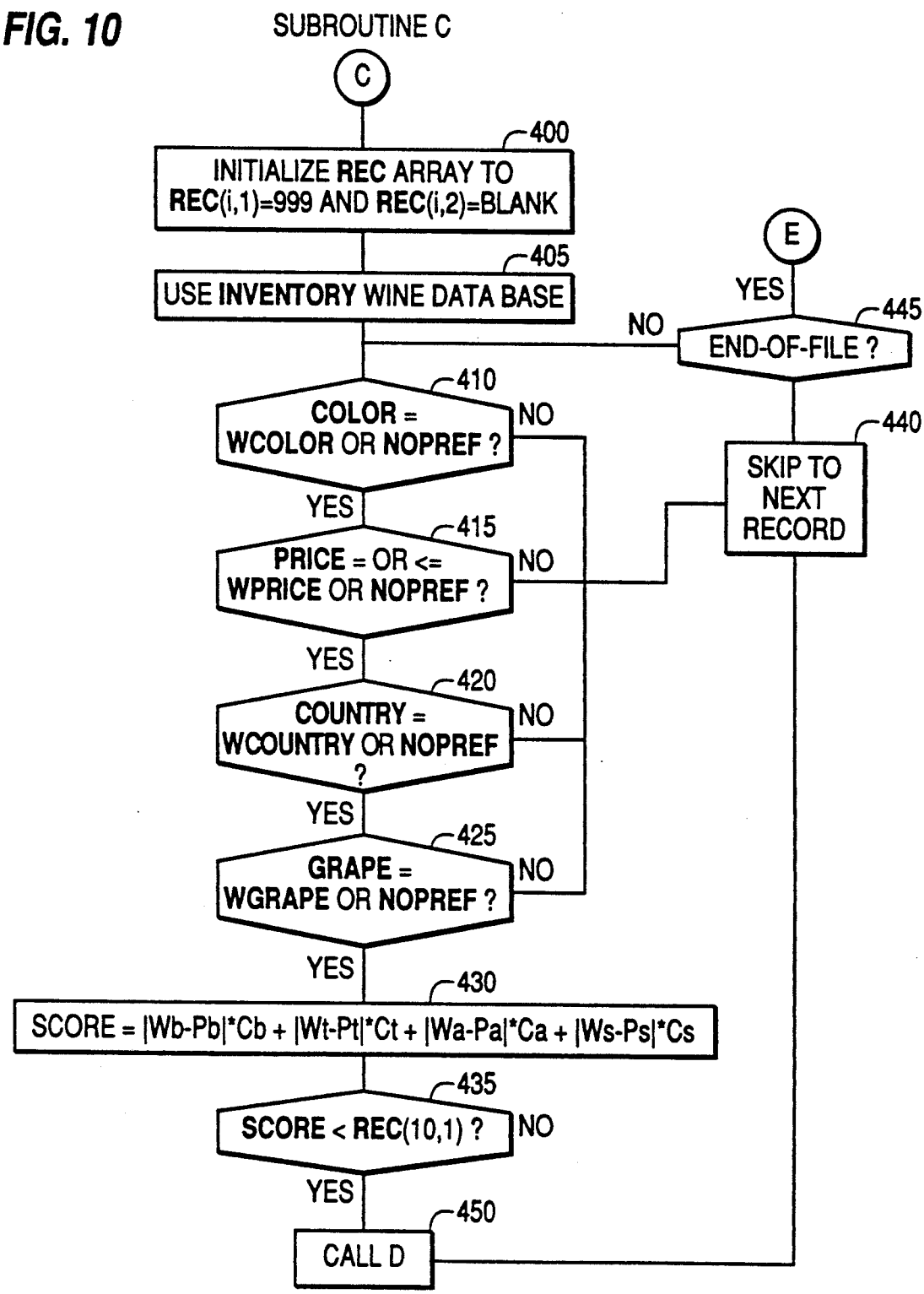
FIG. 10 is a flowchart diagram of a subroutine which selects a wine from an inventory wine list based upon the preference score selected by the FIG. 8 and 9 embodiments.

FIG. 10 is a flowchart diagram of subroutine C which selects a wine from an inventory wine list based on the preference scores selected by the FIGS. 8 and 9 subroutines. Step 400 is an initialization step. The first value REC (i, 1)=999 resets a ranking parameter. REC (i, 2)=blank is a parameter for the wine record number. Since at the initialization stage, no wine has been compared to the preferred parameters, there is no record and it therefore is set to "blank". The variable "i" represents a rank number (1-10 in this example).

Step 405 instructs the program to use an inventory wine database. The inventory wine database is a stored list of wines that are presently in inventory. Each wine has a wine record number so that it may be distinguished from other wines.

Figures 11, 13:
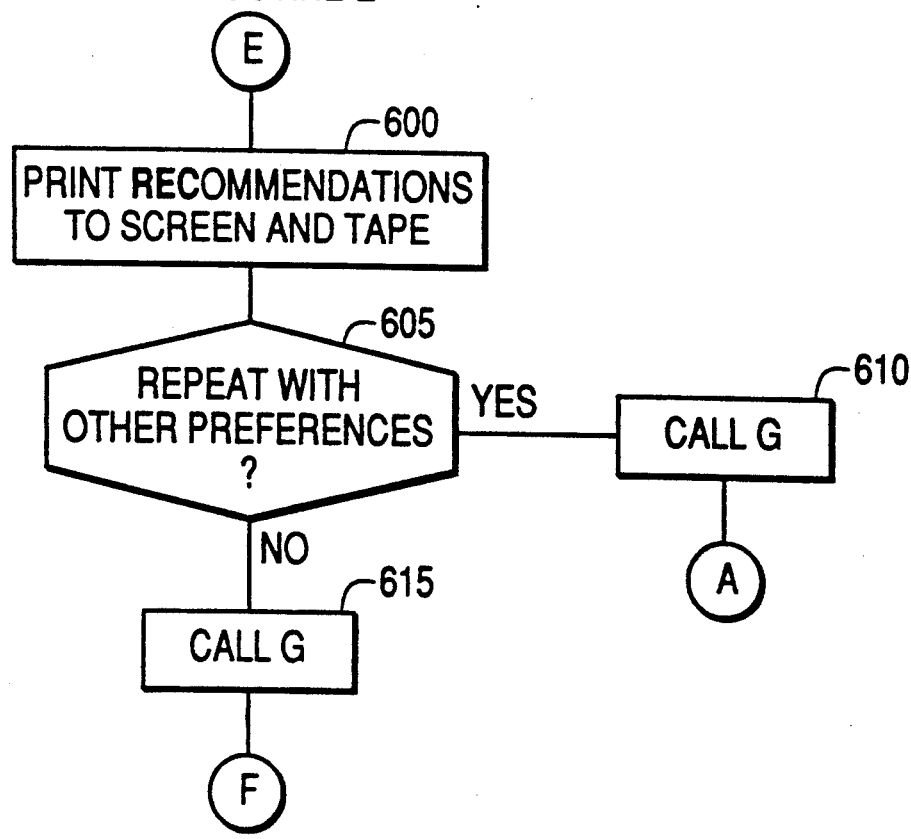
FIG. 11 is a chart showing scale weights used for determining wine rating scores in accordance with the embodiment of FIG. 8.
FIG. 13 is a flowchart diagram of a subroutine for outputting recommended wines and for updating a wine history file in accordance with the embodiment of FIG. 8.

Each wine in the inventory wine database is checked to see if it falls within the selected desired parameters. For example at step 410 the first inventory wine is checked to see if its color (WCOLOR) matches the selected color (COLOR). If the inventory wine color WCOLOR matches the selected color, or if the consumer has indicated no preference for color (NO-PREF), then the inventory wine is next checked for price at step 415. If the inventory wine is not the same as the desired selected color, the subroutine skips to the next record (step 440) and determines if all of the wines in the inventory wine file have been compared with the preferred parameters (step 445). If all of the wines have not been compared, the subroutine goes back to step 410 and begins the checking process again for the next wine on the list. The same sequence takes place for the price parameter (step 415), the country parameter (step 420) and the grape parameter (step 425). If the inventory wine makes it through steps 410-425 without being discarded, this indicates that the wine falls within the input preferences of the customer for a color, price, country and grape. At step 430, the wine is rated by giving it a score (SCORE) based on the following equation:

$$SCORE = (|Wb - Pb| \times Cb) + (|Wt - Pt| \times Ct) + (|Wa - Pa| \times Ca) + (|Ws - Ps| \times Cs) \quad (9)$$

where Wx=wine characteristics from the inventory wine database and Px equals the customer preference for a particular characteristic. FIG. 10A is a flowchart diagram for storing wine characteristics as part of the inventory wine database in accordance with the subroutine of FIG. 10. As in step 111 of the first embodiment, each inventory wine is chemically analyzed at step 431. Then, as in step 161 of the first embodiment, wine characteristics are determined for each inventory wine at step 432 based on the chemical analysis of step 431. Finally, at step 433 wine characteristics determined at step 432 are stored as part of the inventory wine database. FIG. Cx is a scale weight for the body, tannin, acidity and sweetness characteristics of the wine based upon color of the wine, determined by reference to FIG. 11. FIG. 11 is a chart showing the various scale weights used in the above equation for the various characteristics of the wines based on their color. Based upon wine literature and studies done by the applicant, it has been determined that the body, acidity, tannin and sweetness characteristics are of varying importance depending upon the color of the wine. For example, as can be seen in FIG. 11, a white wine has a scale weight of 2 for body, 3 for acidity and sweetness, and 1 for tannin. The low number, e.g., 1 for tannin, indicates that for white wine, tannin is of less importance, or is less of a factor in evaluating wine than is acidity or sweetness which have scale values of 3. These values are used in determining the SCORE value so that each characteristic is given a weighted value of importance roughly equivalent to its value of importance in perception.

Figure 12:
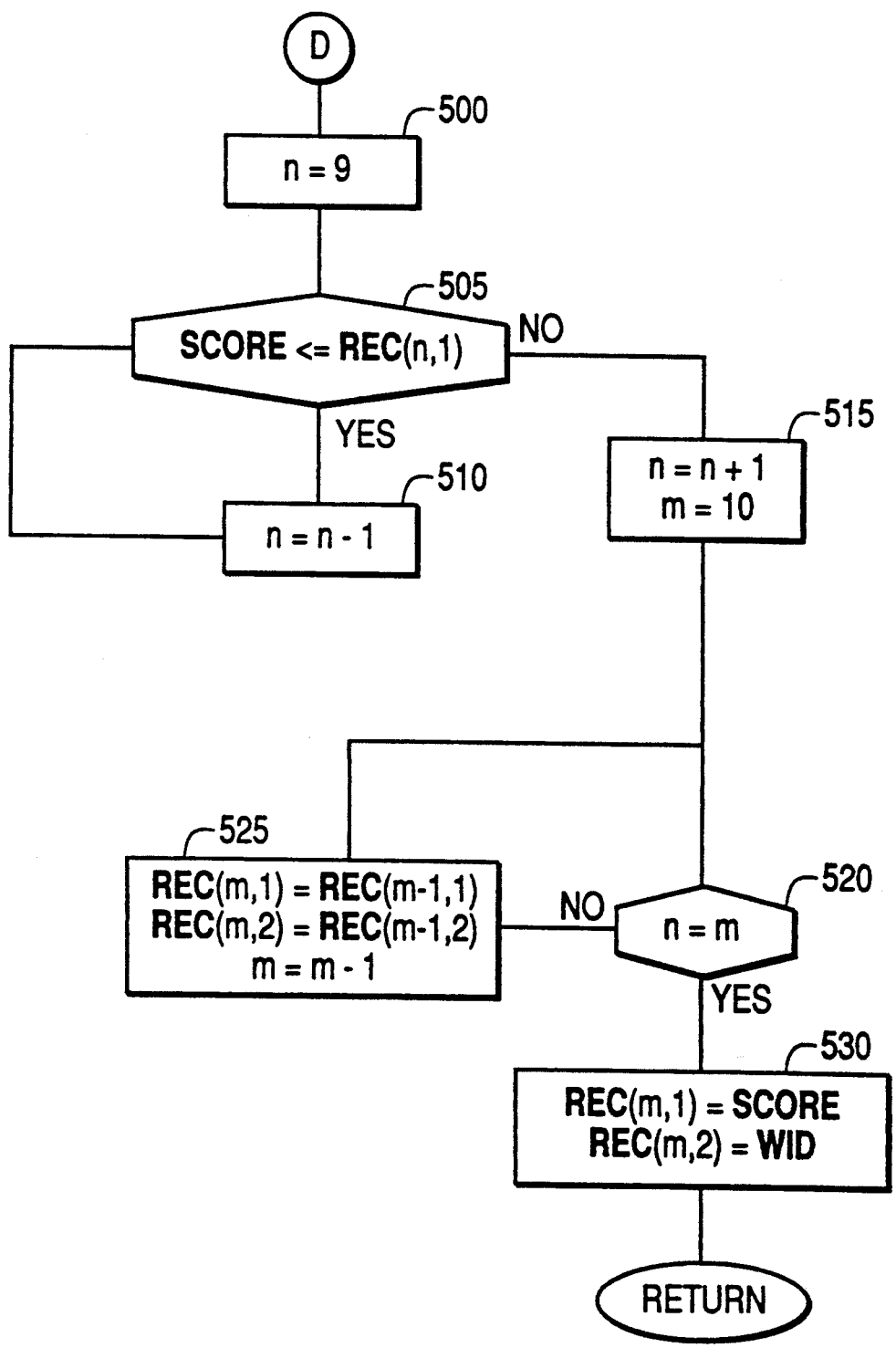
FIG. 12 is a flowchart diagram of a subroutine for ranking selections in sequential order based upon their SCORE values in accordance with the embodiment of FIG. 8.
Figure 15:
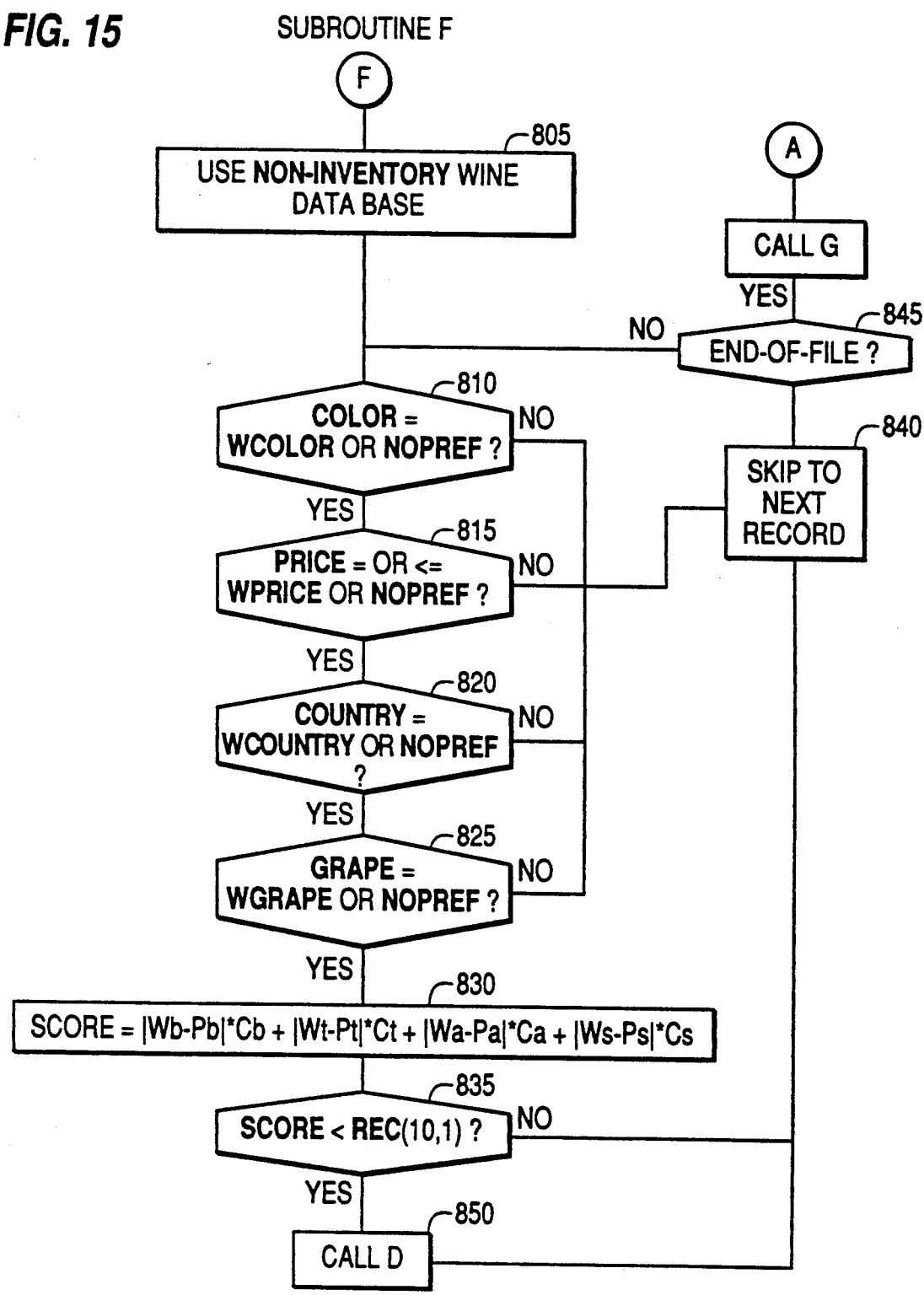
FIG. 15 is a flowchart diagram of a subroutine for selection of potential wine recommendations in accordance with the embodiment of FIG. 8.

A low SCORE indicates that the wine deviates less from the customer preference than a wine having a higher SCORE. The subroutine of FIG. 9 ranks and saves the "best ten" (i=1-10) wines and discards the rest. After a SCORE is determined for the particular inventory wine, it is compared with the tenth ranked record (REC (10, 1)), if such a record exists (step 435). Obviously, the first 10 records checked will all make the best 10 until the 11th record is checked. If the new SCORE is greater than the SCORE for the tenth record, the inventory wine achieving that SCORE is discarded and the next wine in the list is checked (step 440). If, however, the inventory wine SCORE is less than the tenth wine SCORE, then subroutine D (step 450), shown in FIG. 12 is enabled.

Subroutine D determines where in the selected wine file the inventory wine should be placed, and then subroutine D bumps all of the wines with higher SCOREs up one rank. This discards the previous tenth rank wine.

Step 500 sets n equal to 9. This sets up the subroutine D so that it will check the 9th record with the SCORE currently being checked. This check occurs at step 505. If the SCORE is determined to be less than or equal to the ninth record, one is subtracted from n (for example 9−1=8) at step 510 and then the SCORE is checked against the eighth record. This continues until the SCORE is determined to be greater than the SCORE of the record being checked. At this point the routine goes to step 515, where the rank is bumped up by 1 and a value M is set to be equal to the size of the ranking array, in this example, 10. At step 520 n is compared with M to determine if they are equal. If they are not, the routine goes to step 525. Step 525 moves the list upward until the new selection can be inserted in its proper ranking and step 530 inserts the selection in the list. Once all of the wines are placed in proper rank order, the subroutine returns to subroutine C and continues until all the records in the inventory wine database have been checked.

Once the end of the inventory wine list is reached, subroutine E, shown in FIG. 13, prints the recommended wine list (the best ten) to the computer screen and/or a printer (step 600), and then asks the user if there is a wish to repeat the selection process using different preference values (step 605).

In the examples shown in FIG. 13, once a decision is made to repeat or not repeat the wine selection process, the subroutine G, shown in FIG. 14, records a tally of the wines that were selected by the consumer (steps 610 or 615). This is a record keeping function which the store owner can later view to determine, for example, which wines are the most popular. This information can be used for marketing, inventory control and sales strategy.

In FIG. 14, step 700 sets n=1. The variable "n" represents the rank number of the wine in the "best ten" list. At step 710, the rank is checked to see if it equals an initialization number, for example, 999. If the rank is equal to the initialization number, the subroutine G defaults back to subroutine E (step 720). If the rank number is not equal to 999, the subroutine goes to step 730. At step 730, the wine identification number WID is identified and a number WREC, which represents the number of recommendations or potential recommendations for the identified WID, is incremented by 1. This keeps a running count of the number of times the wine was in the "best ten". At step 740, the rank number n is incremented by 1, and then at step 750 it is determined if n is greater than 10. If n is greater than 10, the subroutine reverts back to subroutine E (step 760). If it is less than or equal to 10, the subroutine skips back to step 710 and repeats the process.

As shown in FIG. 13, if the consumer decides not to repeat the wine selection with different preferences, the subroutine F is executed. Subroutine F, shown in FIG. 15, performs essentially the same selection process as in FIG. 9, however, instead of using an inventory wine database (step 805) a non-inventory wine database is used. The purpose of the non-inventory wine database is to inform the store owner of wines that would have been recommended to the consumer had they been in the inventory list. This allows the store owner to make an educated decision regarding which new wines to stock in inventory. The results of the non-inventory wine database subroutine F are also input to the G subroutine, which stores the data for later review by the store owner. The steps 805-850 of FIG. 15 correspond to FIGS. 405-450 of FIG. 9.

With the second embodiment of this invention, a wine consumer can easily make a wine decision based upon quantitative evaluation of the wines available in the store. The consumers can change the parameters in order to experiment with different wines having different characteristics, and do so in a controlled fashion so that they can refine their wine tasting perceptions. In addition, a store owner can keep track of the wines that are good sellers and continue to stock them, and evaluate which wines would have been recommended if they had been in the inventory.

Figure 16:
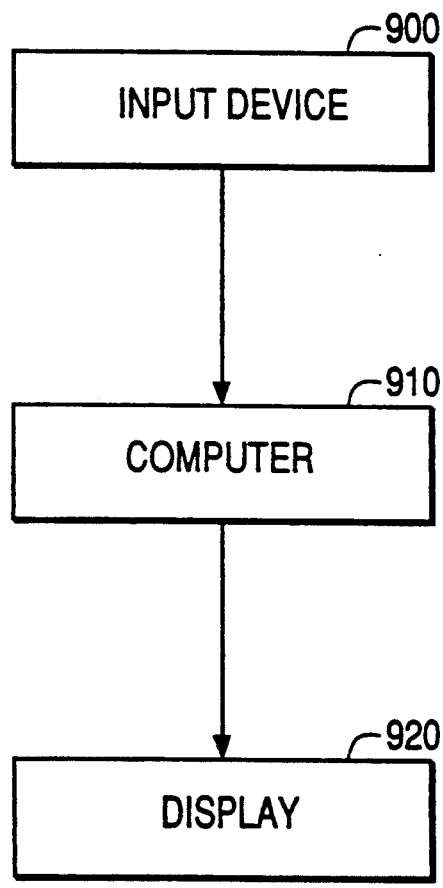
FIG. 16 is a block diagram of an apparatus for performing the method of the second embodiment.

FIG. 16 is a block diagram of an apparatus for performing the method of the second embodiment. A consumer inputs commands at input device 900, which comprises an input means. Input device 900 can be any terminal device, for example a keyboard or touch-pad. Input device 900 is coupled to computer 910. Computer 910 can be any kind of computer, for example, a minicomputer, micro-computer, main-frame, etc. Computer 910 receives the commands input from input device 900 and executes the various subroutines, which are stored by the computer 900. Display 920, which is coupled to computer 910, displays the various screens associated with the subroutines. Display 920 can be any type of display device, for example, a video display terminal, a CRT, etc.

The many features and advantages of the invention are apparent from the detailed specification and thus it is intended by the appended claims to cove all such features and advantages of the invention which fall within the true spirit and scope thereof. Further, since numerous modifications and changes will readily occur to those skilled in the art, it is not desired to limit the invention to the exact construction and operation illustrated and described, and accordingly all suitable modifications and equivalents may be resorted to, falling within the scope of the invention. For example, the disclosed invention is described as being used to evaluate wine. However, this invention can be used in evaluating any liquid that has elements quantifiable by chemical analysis, for example, beer, wine coolers, liquor, detergent, fuel, etc.

What is claimed is:

1. A method for classifying wine to aid an user in selecting a wine, comprising the steps of:
   (a) chemically analyzing a wine sample to determine a first content value based upon an amount of a first constituent in the wine sample;
   (b) determining an objective scale value indicative of a characteristic of the wine sample based upon the first content value; and
   (c) displaying the objective scale value so that the user can make an objective evaluation of the wine sample by viewing the objective scale value.

2. A method as recited in claim 1, further including the step of chemically analyzing the wine sample to determine a second content value based upon an amount of a second constituent in the wine sample, and step (b) further includes the substep of:
   determining the objective scale value further based on the second content value and upon an interaction between the first constituent and the second constituent.

3. A method for classifying wine to aid an user in selecting a wine, comprising the steps of:
   (a) chemically analyzing a wine sample to determine content values, each content value being indicative of an amount of a selected constituent in the wine sample;
   (b) determining objective scale values respectively indicative of characteristics of the wine sample based upon the content values and interactions among selected constituents; and
   (c) simultaneously displaying the objective scale values so that the user can make an objective evaluation of the wine sample by viewing the objective scale value.

4. A method as recited in claim 3, wherein step (a) includes the substeps of determining a content value for tannin Tx and determining a content value for reducing sugar $S_x$, and step (b) includes the substep of determining an astringency scale value $S_T$ in accordance with the following:

if $S_x > 2.0\%$, then $S_T = (0.625 - 0.00313 \ T_x) *(1.4 - 0.2S_x)$; and if $S_x < 2.0\%$, then $S_T = 0.625 - 0.00313 T_x$.

5. A method as recited in claim 3, Wherein step (b) includes the sub-step of:
   determining an alcohol scale value, an acidity scale value, an astringency scale value, a sweetness scale value and a body scale value.

6. A method as recited in claim 5, wherein the alcohol scale value is determined in accordance with the equation $S_{Alc} = 1.43 \times A_x - 11.43$ where $S_{Alc}$ is the alcohol scale value and $A_x$ determined in accordance with the equation $S_s = 2S_x$ where $S_s$ is the sweetness scale value and $S_x$ is the content value for sweetness, the acidity scale value is determined in accordance with the equation $S_{pH}=47.5-12.5 \times pHx$ where $S_{pH}$ is the acidity scale value and pHx is the content value for acidity, the astringency scale value is determined in accordance with the equation $S_T=0.625+0.00313Tx$ where $S_T$ is the astringency scale value and Tx is the content value for astringency, and the body scale value $S_s$ is determined in accordance with one of the following: if the astringency scale value $S_T<4$ and the sweetness scale value $S_s=<3$, then Shd $B=(S_T+S_s+S_{Alc})/3+-(S_{Alc}-5/1.43)+|3-S_T|$; if the astringency scale value $S_T<4$ and the sweetness scale value $S_s>3$, then $S_B=(S_T+S_S+S_{Alc})/3+-(S_{Alc}-5/1.43)+(S_S-3)*0.5+|3-S_T|$; if the astringency scale value $S_T=4$ and the sweetness scale value $S_S=<3$, then $S_B=(S_T+S_s+S_{Alc})/3+(S_{Alc}-5/1.43)+|5-S_T|$; and if the astringency scale value $S_T>=4$ and the sweetness scale value $S_s>3$, then $S_B=(S_T+S_s+S_{Alc})/3+(S_{Alc}-5/1.43)+(S_s-3)*0.5+|5-S_T|$.

7. A method as recited in claim 3, wherein step (a) includes the substeps of determining a content value for reducing sugar $S_x$, determining a content value for acidity pHx and determining a content value for tannin Tx, and step (b) includes the substep of determining a sweetness scale value $S_s$ in accordance with the following:

if $pHs < 3.2$ and $Tx > 2250$ mg/liter,
then $S_S = (2S_X) * (0.3125pHx) * (3 - 0.0009\ Tx)$;
if $pHs < 3.2$ and $Tx = < 2250$ mg/liter,
then $S_S = (2S_X) * (0.3125pHx)$;
if $pHs > 3.2$ and $Tx > 2250$ mg/liter,
then $S_S = (2S_X) * (3 - 0.0009Tx)$: and
if $pHs > 3.2$ and $Tx = < 2250$ mg/liter,
then $S_X = (2Sx)$.

8. A method as recited in claim 7, wherein step (a) further includes the substeps of determining a content value for alcohol Ax, and step (b) further includes the substeps of:

determining an alcohol scale value $S_{Alc\ in\ accordance\ with\ the\ equation}\ S_{Alc}=1.43Ax-11.43$;

determining an acidity scale value $S_{pH}$ in accordance with the equation $S_{pH}=47.5-12.5$ pHx;

determining an astringency scale value $S_T$ in accordance with the following:

if $S_x>2.0\%$, then $S_T=(0.625-0.00313\ Tx)*(1.4-0.28S_x)$, and
if $S_x=<2.0\%$, then $S_T=0.625-0.00313\ Tx$;

determining a body scale value $S_B$ in accordance with the following if $S_T < 4$ and $S_S = < 3$, then
$S_B = (S_T + S_S + S_{Alc})/3 + (S_{Alc} - 5/1.43) + |3 - S_T|$,
if $S_T < 4$ and $S_S > 3$, then
$S_B = (S_T + S_S + S_{Alc})/3 + (S_{Alc} - 5/1.43) + (S_S - 3) * 0.5 + |3 - S_T|$,
if $S_T >= 4$ and $S_S = < 3$, then
$S_B = (S_T + S_S + S_{Alc})/3 + (S_{Alc} - 5/1.43) + |5 - S_T|$,
and
if $S_T >= 4$ and $S_S > 3$, then
$S_B = (S_T + S_S + S_{Alc})/3 + (S_{Alc} - 5/1.43) + (S_S - 3) * 0.5 + |5 - S_T|$; and adjusting the body scale value if $S_{pH}>7.5$ in accordance with the following $S_B=S_B(2-0.133\ S_{pH})$.

9. A method for evaluating a liquid to aid an user in selecting the liquid, comprising the steps of:

(a) chemically analyzing a liquid sample to determine a first content value based upon an amount of a first constituent in the liquid sample;

(b) determining an objective scale value indicative of a characteristic of the liquid sample based upon the first content value; and (c) displaying the objective scale value so that the user can make an objective evaluation of the liquid sample by viewing the objective scale value.

10. A method for aiding an user in selecting wine, comprising the steps of:

(a) analyzing different wines to determine content values, each content value being indicative of the amount of a respective constituent in each wine;

(b) determining a palatability factor for each wine based on the determined content values and interaction among the constituents;

(c) storing the determined palatability factor correlated to the wine from which it was determined in a storage device;

(d) inputting desired palatability factors to said storage device; and (e) outputting a list of wines possessing the input palatability factors so that the user can objectively select one of the wines having the desired palatability factors based on the output list.

11. A method as recited in claim 10, wherein step (b) comprises determining palatability factors for each wine based on the determined content values and interaction among the constituents and determining a ranking SCORE based on the palatability factors for each wine; and step (c) comprises storing the determined palatability factors and each ranking SCORE in the storage device.

12. A method as recited in claim 11, wherein the ranking SCORE for each wine is determined by the following equation:

$$SCORE = (|Wb - Pb| \times Cb) + (|Wt - Pt| \times Ct) + (|Wa - Pa| \times Ca) + (|Ws - Ps| \times Cs)$$

where Wx=the determined palatability factors, Px=the input palatability factors, and Cx=a scale weight for body, tannin, acidity and sweetness.

13. A method of developing a consumer substance evaluation system to aid an user in selecting a substance, comprising the steps of:

(a) determining substance characteristics which influence consumer choice;

(b) determining what substance characteristics can be quantitatively determined; and (c) converting the quantitative determinations into objective product rating scales so that the user can make an objective evaluation of the substance based on the objective product rating scales.

14. A method as recited in claim 13, wherein step (b) further comprises quantitatively determining the characteristics, and step (c) further comprises providing product labels with the product rating scales indicating the quantitative determinations so that the user can make an objective evaluation of the substance by viewing the product labels.

15. An apparatus for classifying wine to aid an user in selecting a wine, comprising:

analysis means for determining constituent values of the wine;

converting means for converting the constituent values to scaled values, said converting means includes means for adjusting the scaled vale for interactions among constituents of the wine; and display means for providing a display of the adjusted scaled values so that the user can make an objective evaluation of the wine by viewing the displayed adjusted scaled values.

16. An apparatus for aiding an user in selecting wine, comprising:

storage means for storing wine records indicating test scaled values of constituent tests;

input means for allowing the user to input preferred scaled values; and comparison means for comparing the preferred scaled values to the test scaled values and indicating to the user the closest match so that the user can objectively select a wine having the test scaled values closest to the preferred scaled values.

17. A wine classification display to aid an user in selecting a wine, comprising:

a first scale having a first indicator indicating a first scaled value based on a first classification constituent of the wine and an interaction between said first classification constituent and a second classification constituent, so that the user can make an objective evaluation of the wine by viewing the first scale.

18. A display as recited in claim 17, further comprising:

a second scale a same size as said first scale having a second indicator indicating a second scaled value of the second classification constituent of the wine, so that the user can make an objective evaluation of the wine by viewing the first and second scales.

19. A display as recited in claim 18, further comprising first and second numerical values corresponding to the first and second scaled values, so that the user can make an objective evaluation of the wine by viewing the first and second scales and the first and second numerical values.

* * * * *